United States Patent
Micheyl

(10) Patent No.: US 10,842,418 B2
(45) Date of Patent: Nov. 24, 2020

(54) METHOD AND APPARATUS FOR TINNITUS EVALUATION WITH TEST SOUND AUTOMATICALLY ADJUSTED FOR LOUDNESS

(71) Applicant: Starkey Laboratories, Inc., Eden Prairie, MN (US)

(72) Inventor: Christophe D. Micheyl, Millery (FR)

(73) Assignee: Starkey Laboratories, Inc., Eden Prairie, MN (US)

( * ) Notice: Subject to any disclaimer, the term of this patent is extended or adjusted under 35 U.S.C. 154(b) by 358 days.

(21) Appl. No.: 14/858,982

(22) Filed: Sep. 18, 2015

(65) Prior Publication Data

US 2016/0089060 A1    Mar. 31, 2016

Related U.S. Application Data

(60) Provisional application No. 62/056,980, filed on Sep. 29, 2014.

(51) Int. Cl.
*A61B 5/12* (2006.01)
*A61B 5/00* (2006.01)

(52) U.S. Cl.
CPC .............. *A61B 5/128* (2013.01); *A61B 5/123* (2013.01); *A61B 5/72* (2013.01)

(58) Field of Classification Search
None
See application file for complete search history.

(56) References Cited

U.S. PATENT DOCUMENTS

| | | | |
|---|---|---|---|
| 6,155,971 A | * | 12/2000 | Calhoun ................ A61B 5/121 600/28 |
| 6,370,255 B1 | | 4/2002 | Schaub et al. |
| 6,974,410 B2 | | 12/2005 | Micheyl et al. |
| 7,010,133 B2 | | 3/2006 | Chalupper et al. |
| 7,081,085 B2 | * | 7/2006 | Viirre .................. A61B 5/0482 600/28 |
| 8,014,870 B2 | | 9/2011 | Seidman |

(Continued)

FOREIGN PATENT DOCUMENTS

| | | |
|---|---|---|
| CA | 2581810 C | 5/2006 |
| EP | 0836363 B1 | 9/2003 |

(Continued)

OTHER PUBLICATIONS

"European Application Serial No. 15187063.1, Communication Pursuant to Article 94(3) EPC dated Oct. 12, 2017", 5 pgs.

(Continued)

*Primary Examiner* — Patrick Fernandes
*Assistant Examiner* — Benjamin S Melhus
(74) *Attorney, Agent, or Firm* — Schwegman Lundberg & Woessner, P.A.

(57) ABSTRACT

A system for psychoacoustic evaluation of tinnitus synthesizes a test sound that is customized for a patient using the patient's audiogram, a model of the tinnitus related to the patient's audiogram, a psychoacoustic loudness model, and various test-sound parameters. In various embodiments, the system automatically adjusts the intensity and spectral level of the test sound such that the intensity of the test sound as perceived by the patient remains approximately constant across various frequencies and/or sound types used in the psychoacoustic evaluation of tinnitus.

20 Claims, 3 Drawing Sheets

(56) References Cited

U.S. PATENT DOCUMENTS

| | | | |
|---|---|---|---|
| 8,088,077 B2 | 1/2012 | Turner et al. | |
| 8,213,624 B2 | 7/2012 | Seefeldt | |
| 8,353,846 B2* | 1/2013 | Henry | A61B 5/7435 |
| | | | 600/559 |
| 9,138,178 B2* | 9/2015 | Lee | A61B 5/128 |
| 2006/0167335 A1 | 7/2006 | Park et al. | |
| 2008/0253586 A1 | 10/2008 | Wei | |
| 2010/0098276 A1 | 4/2010 | Frohlich et al. | |
| 2011/0105967 A1* | 5/2011 | Zeng | A61M 21/00 |
| | | | 601/47 |
| 2011/0137111 A1 | 6/2011 | Hanley et al. | |
| 2012/0283593 A1* | 11/2012 | Searchfield | H04R 25/75 |
| | | | 600/559 |
| 2013/0163797 A1 | 6/2013 | Suzman et al. | |
| 2013/0338527 A1 | 12/2013 | Suh et al. | |
| 2014/0146986 A1 | 5/2014 | Ypma et al. | |
| 2016/0030245 A1* | 2/2016 | Perry | H04R 25/75 |
| | | | 600/28 |

FOREIGN PATENT DOCUMENTS

| | | |
|---|---|---|
| EP | 2002539 B1 | 12/2010 |
| EP | 2693637 A1 | 2/2014 |
| WO | WO-0242986 A1 | 5/2002 |
| WO | WO-2008011396 A2 | 1/2008 |
| WO | WO-2012066149 A1 | 5/2012 |

OTHER PUBLICATIONS

"European Application Serial No. 15187063.1, Extended European Search Report dated Dec. 18, 2015", 8 pgs.

Chen, ZL, et al., "A new method of calculating auditory excitation patterns and loudness for steady sounds", Hear Res. 2011 282(1-2), (2011), 204-215.

Chen, ZL, et al., "A new model for calculating auditory excitation patterns and loudness for cases of cochlear hearing loss", Hear Res. 282(1-2), (2011), 69-80.

"European Application Serial No. 15187063.1, Response filed Feb. 21, 2018 to Communication Pursuant to Article 94(3) EPC dated Oct. 12, 2017", 16 pgs.

"European Application Serial No. 15187063.1, Communication Pursuant to Article 94(3) EPC dated Jun. 27, 2019", 6 pgs.

* cited by examiner

METHOD AND APPARATUS FOR TINNITUS EVALUATION WITH TEST SOUND AUTOMATICALLY ADJUSTED FOR LOUDNESS

CLAIM OF PRIORITY

The present application claims the benefit of priority under 35 U.S.C. § 119(e) of U.S. Provisional Patent Application Ser. No. 62/056,980, filed on Sep. 29, 2014, which application is incorporated herein by reference in its entirety.

TECHNICAL FIELD

This document relates generally to audio systems and more particularly to a system for psychoacoustic evaluation of tinnitus with a test sound automatically adjusted for loudness across various frequencies.

BACKGROUND

Tinnitus is a condition in which a patient perceives a sound in the ears in absence of a corresponding external sound. While ringing in the ears is associated with tinnitus, other types of sounds can be perceived and can be sporadic, intermittent or continuous. Tinnitus can be caused by various conditions or injuries, but regardless of cause can be debilitating and decrease a patient's quality of life.

Because tinnitus has different causes and symptoms, and different patients may perceive different sounds in the ears, its diagnosis includes characterizing the tinnitus for each individual patient. As part of a diagnostic procedure, for example, a clinician may play various sounds to a patient complaining about tinnitus, and the patient identifies the sound that most closely matches his or her tinnitus. Subsequently, treatment may be determined for the patient based on the identified characteristics (such as frequencies) of the tinnitus.

SUMMARY

A system for psychoacoustic evaluation of tinnitus synthesizes a test sound that is customized for a patient using the patient's audiogram, a model of the tinnitus related to the patient's audiogram, a psychoacoustic loudness model, and various test-sound parameters. In various embodiments, the system automatically adjusts the intensity and spectral level of the test sound such that the intensity of the test sound as perceived by the patient remains approximately constant across various frequencies and/or sound types used in the psychoacoustic evaluation of tinnitus.

In one embodiment, the system includes a sound generation device and a sound delivery device. The sound generation device including a processing circuit that can be configured to determine a power spectrum of a test sound using an audiogram of the patient, test-sound parameters, a model of a spectrum of tinnitus related to the audiogram of the patient, and a psychoacoustic loudness model, and to produce an output sound signal representing the test sound using the power spectrum, such that the test sound has an approximately constant loudness as perceived by the patient across various frequencies to be evaluated. The sound delivery device produces the test sound based on the output sound signal and delivers the sound to the patient.

In one embodiment, the system includes a processing circuit that can be configured to synthesize a test sound. The processing circuit includes an audiogram input, a test parameter input, a power spectrum analyzer, and a test sound synthesizer. The audiogram input receives a pure-tone audiogram of the patient. The test parameter input receives test-sound parameters. The power spectrum analyzer determines a power spectrum of the test sound using the pure-tone audiogram of the patient, the test-sound parameters, a tinnitus-spectrum model, and a loudness model. The test sound synthesizer produces an output sound signal representing the test sound based on the power spectrum, such that the test sound has an intensity and a spectral level that provide an approximately constant loudness as perceived by the patient across various frequencies to be evaluated.

In one embodiment, a method for psychoacoustic evaluation of tinnitus for a patient is provided. A test sound customized for the patient is synthesized using an audiogram of the patient, test-sound parameters, a model of a spectrum of tinnitus related to the audiogram of the patient, and a psychoacoustic loudness model. The test sound has an approximately constant loudness as perceived by the patient across various frequencies to be evaluated. The test sound is delivered to ears of the patient for the psychoacoustic evaluation of tinnitus.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
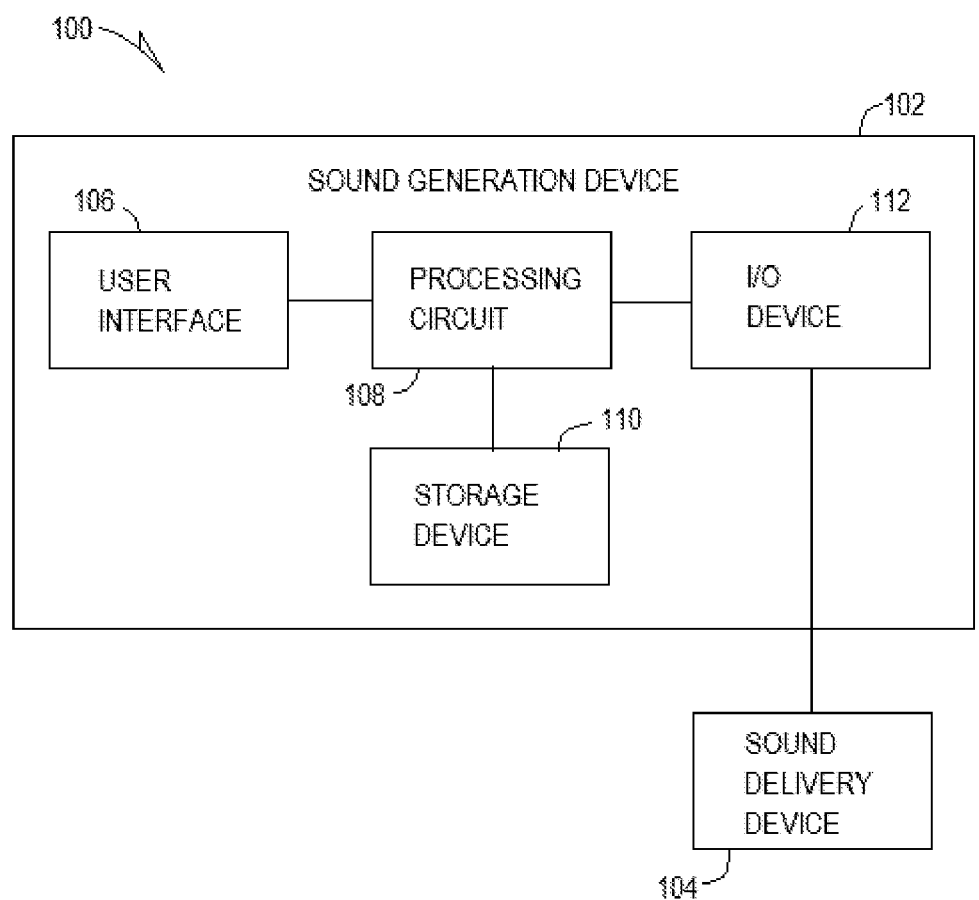
FIG. 1 is a block diagram illustrating an embodiment of a system for psychoacoustic evaluation of tinnitus.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, a system for psychoacoustic evaluation of tinnitus with a test sound that is automatically adjusted for loudness at various frequencies. To measure tinnitus for a patient, a clinician may present a test sound with varying characteristics to that patient. The test sound may include, for example, tones at different frequencies and/or noises of various bandwidths and center frequencies. As the test sound changes across presentations during testing (for instance, the sound changes from a pure-tone to a noise, or from a pure tone having a first frequency to a pure-tone having a second frequency), its overall level (or intensity) and/or spectrum (spectral level as a function of frequency) may need to be readjusted so that the loudness (i.e., perceived sound intensity) remains approximately constant for the patient. In addition, the spectrum of the test sound may need to be appropriately shaped such that spectral components that are intended to be perceived by the patient do not fall below the patient's absolute hearing threshold. When the level and/or spectrum are not adjusted properly, the test sounds can become too soft (and possibly inaudible) or too loud for the patient, or the test sound may no longer sound like the tinnitus, making it difficult for the patient to compare the test sound to his or her tinnitus. This can result in substantial testing difficulties for the patient and for the clinician, including, for example, longer testing times and unreliable test results. The need for the clinician to readjust the intensity and spectra of the test sound frequently during tinnitus measurements is an important reason for which a tinnitus measurement using existing tools (such as an audiometer or software applications on a computer) is often a tedious and time-consuming task for clinicians.

In examples of such existing tools for tinnitus measurement, the user, including the clinician and/or the patient, needs to either adjust the sound level at the beginning of the test, in such a way that sounds remain audible and are not too loud throughout the entire frequency range, or adjust the sound volume (or intensity) whenever needed during the test. However, manually adjusting the sound level once at the beginning for the entire test is impractical when the patient under test has steeply sloping hearing loss (which is not rare for tinnitus patients), such that a sound of a given volume (e.g., 50 dB above threshold at 500 Hz) can be too loud compared to the tinnitus at one frequency (e.g., 500 Hz) but barely audible at another (e.g. 4000 Hz). Manually readjusting the volume as often as needed, on the other hand, is cumbersome for the clinician, distractive for the patient, and time-consuming for both the clinician and the patient. Another limitation of these two approaches is that they do not include spectral shaping based on the patient's individual audiogram, to ensure that the spectral components that are intended to be heard by the patient (such as high-frequency components) are indeed audible to the patient. For instance, when playing a broadband noise at 20 dB sound pressure level (SPL) overall level to a patient who has a threshold of 60 dB hearing level (HL) at 4 kHz, high frequency components of the noise are not audible for that patient. For this reason, the resulting percept may not sound like the tinnitus, which often contains a predominance of high-frequency components.

The present subject matter solves the problems of such existing tinnitus measurement tools, including those discussed above, by using a loudness model and a model of tinnitus sounds, in combination with the patient's pure-tone audiogram, to automatically adjust the overall level and spectra of test sounds, so that their overall and specific loudness is adequate for the purpose of characterizing tinnitus, despite changes in the stimulus type (pure-tone, narrowband, or broadband) and frequency (or center frequency). In various embodiments, the present system includes a sound generation device that automatically adjusts the intensity and spectral shape of a test sound based on the patient's audiogram, using a psychoacoustic loudness model and a model of the tinnitus related to the patient's audiogram. The test sound is to be presented in the context of a psychoacoustic tinnitus-evaluation test performed on the patient. The test sound is adjusted so that (1) the loudness of the sound remains approximately constant for the patient through the presentation of the test sound, thus avoiding or reducing the need for the clinician to manually readjust sound intensity whenever the frequency and/or type of the test sound change, and (2) spectral components that are likely to contribute significantly to perceived similarity between the test sound and the tinnitus are audible (or most likely audible) for the patient. Unique aspects of the present system include use of a loudness model, in conjunction with a model of the tinnitus spectrum in relation to the patient's audiogram and individual audiometric information (patient's pure-tone audiogram), for automatically adjusting the spectral level of test sounds presented in the context of a test of psychoacoustic characteristics of tinnitus.

The present system is advantageous over existing tinnitus measurement tools in its practical applications. For example, when compared to the existing tools as discussed above, the present system makes the test easier (i.e., less effortful and less tedious) for the clinician, and makes the test faster because no, or less, time is spent on readjusting sound intensity as the test progresses. By making the test easier and faster, tests using the present system may also result in more accurate results. Additionally, by ensuring audibility of spectral components that might otherwise not be detectable by the patient under test, the present system is likely to produce sounds that are perceived as more similar to the tinnitus than existing tools that do not incorporate such overall and spectral-level adjustments. Such advantages and benefits are indicated to be likely borne out in clinical applications by preliminary results obtained in the context of a clinical evaluation of a prototype of the present system.

FIG. 1 is a block diagram illustrating an embodiment of a system 100 for psychoacoustic evaluation of tinnitus. System 100 includes a sound generation device 102 and a sound delivery device 104. In various embodiments, the system 100 may be used by a user such as a clinician who evaluates a patient complaining about tinnitus or be used by the patient to evaluate his or her own tinnitus.

Sound generation device 102 includes a user interface 106, a processing circuit 108, a storage device 110, and an input/output (I/O) device 112. User interface 106 presents information to the user and receives commands and other information from the user, such as information identifying the patient and testing commands and results for the patient. Processing circuit 108 synthesizes a test sound to be used in the psychoacoustic evaluation of tinnitus that is customized for the patient, by using the patient's audiogram, a model of a spectrum of tinnitus related to the patient's audiogram, a psychoacoustic loudness model, and various test-sound parameters. In various embodiments, processing circuit 108 is configured to automatically adjust the intensity and spectral level of a test sound across various frequencies and/or sound types (tone, narrowband noise, broadband noise, etc.) so that the level (loudness) of the test sound as perceived by the patient remains approximately constant, and so that spectral components that are likely to contribute significantly to perceived similarity between the test sound and the tinnitus of the patient and are most likely to be audible to the patient. Storage device 110 stores various information used by processing circuit 108 in the synthesis of the test sound, such as the patient's audiogram and test sound parameters. I/O device 112 includes one or more input and/or output ports to allow sound generation device to receive information such as the patient's audiogram and various parameters and/or models used in the synthesis of the test sound, and delivers the test sound to sound delivery device 104 in the form of a time-domain electrical signal. In various embodiments, processing circuit 108 produces an output sound signal representing the synthesized test sound to be transmitted to sound delivery device 104 via I/O device 112. In one embodiment, sound generation device 102 communicates with sound delivery device 104 via a wired link through which the output sound signal is transmitted. In another embodiment, sound generation device 102 communicates with sound delivery device 104 via a wireless link through which the output sound signal is transmitted.

Sound delivery device 104 produces the test sound based on the output sound signal and delivers to sound to the ears of the patient. In various embodiments, sound delivery device 104 can include any acoustic transducer that is capable of converting the output sound signal to the test sound. In one embodiment, sound delivery device 104 includes a headphone (set of earphones). In another embodiment, sound delivery device 104 includes a pair of hearing aids. In another embodiment, sound delivery device 104 includes one or more speakers. In one embodiment, sound delivery device 104 delivers the test sound to the patient in a soundproof room during the psychoacoustic evaluation of tinnitus. In another embodiment, sound delivery device 104 delivers the test sound to the patient in any suitable environments, including the patient's home, during the psychoacoustic evaluation of tinnitus.

In various embodiments, the circuit of each device discussed in this document is implemented using hardware, software, firmware or a combination of hardware, software and/or firmware. In various embodiments, processing circuit 108 may be implemented using one or more circuits specifically constructed to perform one or more functions discussed in this document or one or more general-purpose circuits programmed to perform such one or more functions. Examples of such general-purpose circuit can include a microprocessor or a portion thereof, a microcontroller or portions thereof, and a programmable logic circuit or a portion thereof.

Figure 2:
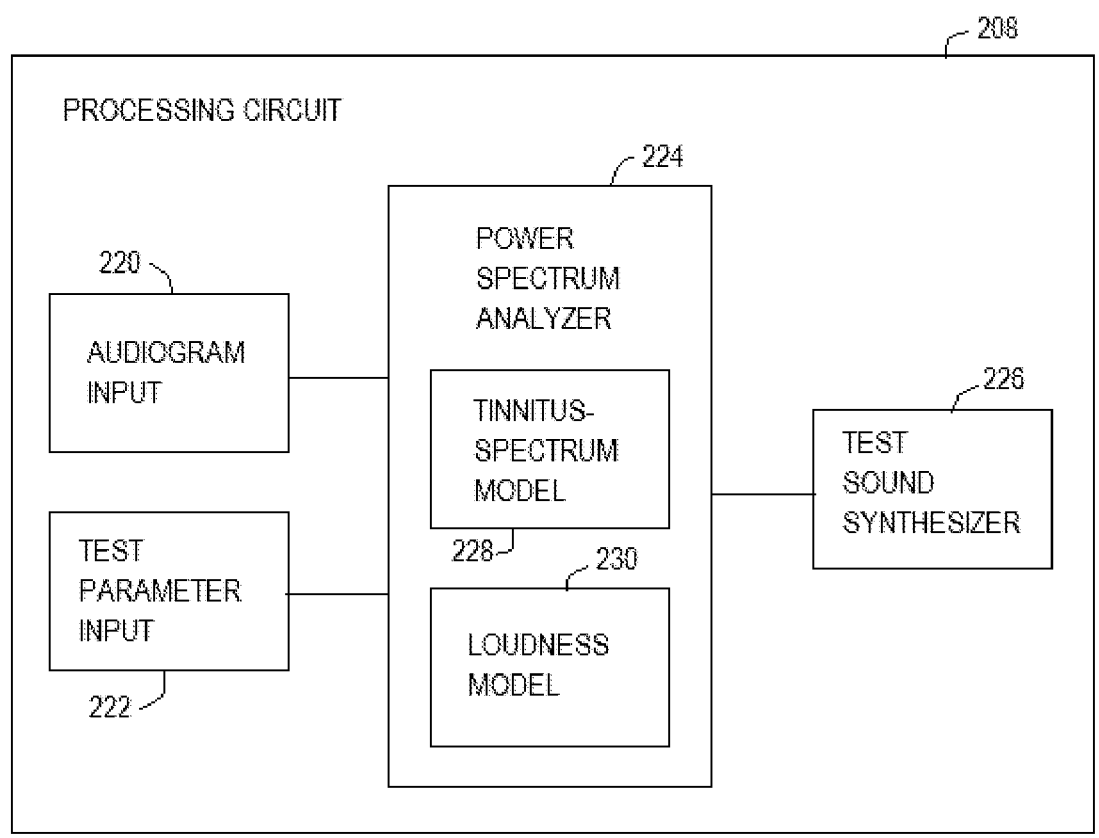
FIG. 2 is a block diagram illustrating an embodiment of a processing circuit of the system for psychoacoustic evaluation of tinnitus.
Figure 3:
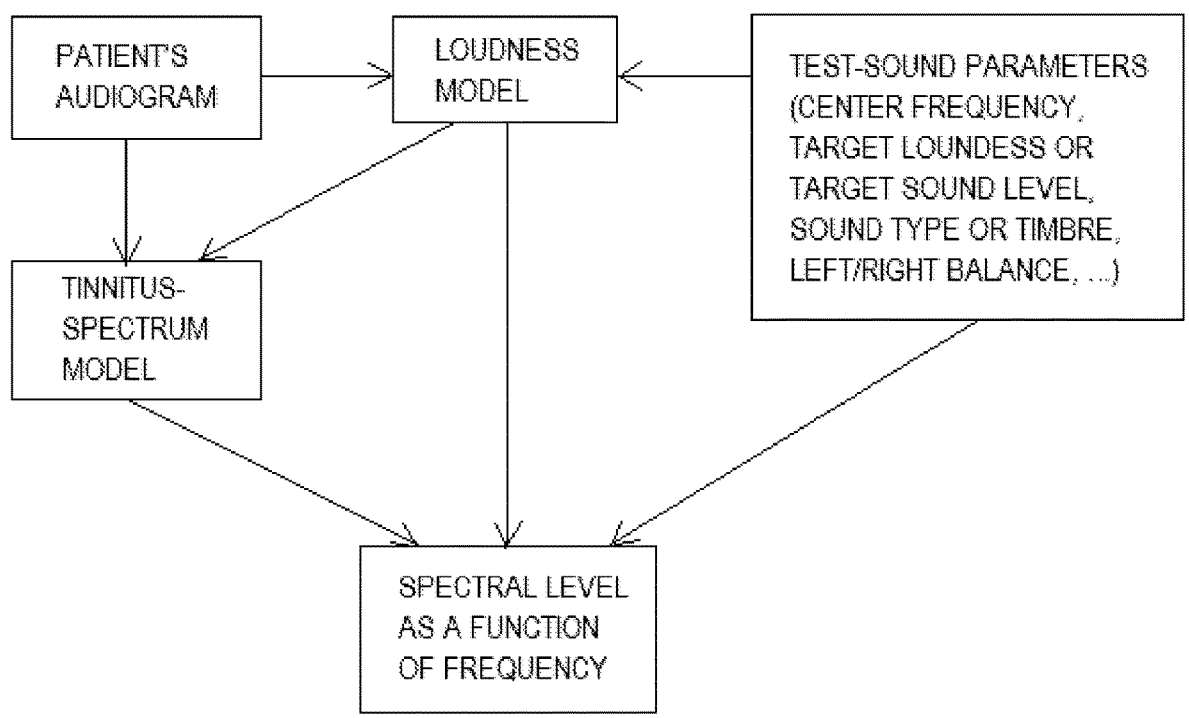
FIG. 3 is an illustration of an embodiment of a schema of operation of the processing circuit.

FIG. 2 is a block diagram illustrating an embodiment of a processing circuit 208, which represent an embodiment of processing circuit 108. FIG. 3 is a block diagram illustrating an embodiment of a schema of operation of processing circuit 208.

Processing circuit 208 includes an audiogram input 220, a test parameter input 222, a power spectrum analyzer 224, and a test sound synthesizer 226. Audiogram input 220 receives the patient's pure-tone audiogram, such as from storage device 110 or I/O device 112. Test parameter input 222 receives test-sound parameters, such as from storage device 110 or user interface 106. Examples of test-sound parameters include center frequency, target loudness or target sound level, sound type or timbre, and left/right balance. Power spectrum analyzer 224 uses the patient's pure-tone audiogram and the test-sound parameters, in conjunction with a tinnitus-spectrum model 228 and a loudness model 230, to determine the power spectrum (spectral level as a function of frequency) of the test sound. Test sound synthesizer 226 produces the output sound signal, which is a time-domain electrical signal representing the test sound, based on the power spectrum determined by power spectrum analyzer 224. The test sound has an intensity and a spectral level across various frequencies and/or sound types to be tested that provide an approximately constant level (loudness) as perceived by the patient. The spectral components of the test sound are likely to contribute significantly to perceived similarity between the test sound and the tinnitus of the patient and are most likely to be audible to the patient.

In various embodiments, tinnitus-spectrum model 228 includes a nonlinear transformation of the patient's absolute pure-tone hearing thresholds. For example, the tinnitus power spectrum is estimated as sigmoid transformation of absolute hearing thresholds, such that the specific loudness of the tinnitus increases as a monotonic function of hearing loss but saturates for higher degrees of loss. Alternatively or additionally, the tinnitus power spectrum may be computed as a nonlinear monotonic transformation of the energy at the output of model auditory filters (e.g., equivalent rectangular bands or roexp functions) in response to a bandlimited noise signal amplified according to the hearing loss. Loudness model 230 simulates a person's auditory system from the ears to the brain to estimate the level (loudness) of a sound as perceived by the person. An example of the loudness model is discussed in Chen Z L, Hu G, Glasberg B R, Moore B C. (2011) A new method of calculating auditory excitation patterns and loudness for steady sounds. Hear Res. 2011 282(1-2):204-215 and Chen Z L, Hu G, Glasberg B R, Moore B C. (2011) A new model for calculating auditory excitation patterns and loudness for cases of cochlear hearing loss. Hear Res. 282(1-2):69-80.

A prototype of system 100 has been evaluated with nine patients. The results of this evaluation confirm that testing with system 100 is easy to use for the tester and the patient, fast (each measurement usually took less than 5 minutes), reliable (for most patients, test/retest variability was within measurement resolution), and effective (most patients reported that the sounds presented to them at the end of the procedure sounded "exactly" or "almost exactly" like their tinnitus). Outcome of the evaluation provides, among other things, some indication that, by automatically shaping and adjusting the spectrum level of test sounds used for assessing tinnitus, the present subject matter may contribute to substantially facilitate clinical evaluations of tinnitus, especially in listeners with hearing loss.

In various embodiments, system 100 can be configured for use by clinicians who perform the psychoacoustic evaluation of tinnitus, and/or configured for automating tinnitus measurement directly by the end-user (patients). In various embodiment, sound generation device 102 may be implemented as a dedicated device or in another device such as a desktop computer, laptop computer, tablet computer, or smartphone.

In various embodiments, sound delivery device 104 can be any device capable of producing the test sound using the output sound signal produced by sound generation device 102. Examples of such device include, but are not limited to, headphone, earphones, ear buds, and hearing aids. Examples of such hearing aids include, but are not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used with hearing assistance devices generally, such as cochlear implant type hearing devices. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A system for psychoacoustic evaluation of tinnitus for a patient having an auditory system, comprising:
 a sound generation device including a processing circuit configured to:
  determine a power spectrum of a test sound using an audiogram of the patient, test-sound parameters, a model of a spectrum of tinnitus being a nonlinear transformation of absolute pure-tone hearing thresholds of the patient, and a psychoacoustic loudness model simulating the patient's auditory system to estimate loudness of a sound as perceived by the patient, the test sound to be compared to tinnitus of the patient during the psychoacoustic evaluation of tinnitus and including various frequencies and sound types to be evaluated for characterizing the tinnitus of the patient; and
  produce an output sound signal representing the test sound using the power spectrum, such that the test sound is automatically adjusted to have a constant loudness as perceived by the patient across the various frequencies and sound types to be evaluated to ensure that spectral components of the test sound likely contributing to perceived similarity between the test sound and the tinnitus of the patient are audible to the patient; and
 a sound delivery device configured to:
  produce the test sound using the output sound signal; and
  deliver the test sound to the patient.

2. The system of claim 1, wherein the sound delivery device comprises hearing aids.

3. The system of claim 1, wherein the sound delivery device comprises ear buds.

4. The system of claim 1, wherein the sound delivery device comprises headphones.

5. The system of claim 1, wherein the spectrum of tinnitus is estimated as a sigmoid transformation of the absolute pure-tone hearing thresholds of the patient.

6. The system of claim 1, wherein the test-sound parameters comprise a center frequency, a target loudness, a sound type or timbre, and a left/right balance.

7. The system of claim 1, wherein the sound generation device comprises a smartphone.

8. The system of claim 1, wherein the sound delivery device is configured to be communicatively coupled to the sound generation device via a wireless link.

9. The system of claim 1, wherein the sound delivery device comprises hearing assistance devices.

10. The system of claim 9, wherein the hearing assistance devices comprises hearing aids.

11. The system of claim 1, wherein the sound delivery device comprises one or more speakers.

12. A system for evaluating tinnitus for a patient having an auditory system, comprising:
 a processing circuit configured to synthesize a test sound used for the evaluation of tinnitus including comparing the test sound to tinnitus of the patient, the test sound including various frequencies and sound types to be evaluated for characterizing the tinnitus of the patient by the comparison, the processing circuit including:
  an audiogram input configured to receive a pure-tone audiogram of the patient;
  a test parameter input configured to receive test-sound parameters;
  a power spectrum analyzer configured to determine a power spectrum of the test sound using the pure-tone audiogram of the patient, the test-sound parameters, a tinnitus-spectrum model being a nonlinear transformation of absolute pure-tone hearing thresholds of the patient, and a psychoacoustic loudness model configured for simulating the patient's auditory system to estimate loudness of a sound as perceived by the patient; and
  a test sound synthesizer configured to produce an output sound signal representing the test sound based on the power spectrum, such that the test sound has an intensity and a spectral level automatically adjusted to provide a constant loudness as perceived by the patient across the various frequencies and sound types to be evaluated, the constant loudness ensuring that spectral components of the test sound likely contributing to perceived similarity between the test sound and the tinnitus of the patient are audible to the patient; and
 a sound delivery device configured to receive the output sound signal from the processing circuit via a wireless link, to produce the test sound based on the output sound signal, and to deliver the test sound to the patient.

13. The system of claim 12, wherein the sound delivery device comprises one or more speakers configured to produce the test sound based on the output sound signal and deliver the test sound to the patient.

14. The system of claim 13, wherein the nonlinear transformation of the absolute pure-tone hearing thresholds of the patient is estimated as a sigmoid transformation of the absolute pure-tone hearing thresholds of the patient.

15. The system of claim 14, wherein the test-sound parameters comprise a center frequency, a target loudness, a sound type or timbre, and a left/right balance.

16. The system of claim 12, wherein the sound delivery device comprises hearing aids configured to produce the test sound based on the output sound signal and deliver the test sound to the patient.

17. The system of claim 12, wherein the sound delivery device comprises headphones configured to produce the test sound based on the output sound signal and deliver the test sound to the patient.

18. The system of claim 12, wherein the sound delivery device comprises ear buds configured to produce the test sound based on the output sound signal and deliver the test sound to the patient.

19. The system of claim 12, comprising a sound generation device configured to be communicatively coupled to the sound delivery device and including the processing circuit, the sound generation device including a computer or a smartphone.

20. The system of claim 19, wherein the sound generation device is configured to be communicatively coupled to the sound delivery device via a wireless link.

* * * * *